United States Patent [19]

Mehta

[11] Patent Number: 5,084,278

[45] Date of Patent: Jan. 28, 1992

[54] TASTE-MASKED PHARMACEUTICAL COMPOSITIONS

[75] Inventor: Atul M. Mehta, Ramsey, N.J.

[73] Assignee: Nortec Development Associates, Inc., Ramsey, N.J.

[21] Appl. No.: 360,663

[22] Filed: Jun. 2, 1989

[51] Int. Cl.$^5$ .................... A61K 9/50; A61K 9/58; A61K 9/62

[52] U.S. Cl. .................. 424/441; 424/489; 424/490; 424/494; 424/495; 424/497; 514/963; 514/974

[58] Field of Search ............ 424/441, 489, 490, 494, 424/495, 497, 457, 468; 514/963, 974

[56] References Cited

U.S. PATENT DOCUMENTS

| | | | |
|---|---|---|---|
| 2,702,264 | 2/1955 | Klaui | 167/82 |
| 3,030,273 | 4/1962 | Zagnoli | 167/82 |
| 3,033,754 | 5/1962 | Krahnke | 167/82 |
| 3,070,509 | 12/1962 | Volker et al. | 167/82 |
| 3,453,360 | 7/1969 | Hill | 424/22 |
| 3,520,970 | 7/1970 | Lehmann et al. | 424/25 |
| 3,531,418 | 4/1970 | Fanger | 252/316 |
| 3,576,760 | 4/1971 | Gould | 252/403 |
| 3,577,512 | 5/1971 | Shepherd | 424/22 |
| 3,629,392 | 12/1971 | Banker et al. | 424/22 |
| 3,775,537 | 11/1973 | Lehmann et al. | 424/21 |
| 3,821,422 | 6/1974 | Morse et al. | 426/72 |
| 3,860,733 | 1/1975 | Morse et al. | 426/302 |
| 3,909,444 | 9/1975 | Anderson | 252/316 |
| 3,935,326 | 1/1976 | Groppenbacher | 427/3 |
| 3,959,540 | 5/1976 | Leiberich | 424/35 |
| 4,016,254 | 4/1977 | Seager | 424/33 |
| 4,060,598 | 11/1977 | Groppenbacher | 424/33 |
| 4,101,651 | 7/1978 | Kobayashi et al. | 424/35 |
| 4,112,215 | 9/1978 | Boessler | 528/503 |
| 4,321,117 | 3/1982 | Kaetsu | 204/159.16 |
| 4,321,253 | 3/1982 | Beatty | 424/35 |
| 4,330,338 | 5/1982 | Banker | 106/197 C |
| 4,341,759 | 7/1982 | Bogentoft | 424/21 |
| 4,367,217 | 1/1983 | Gruber | 424/19 |
| 4,411,754 | 10/1983 | Kaetsu | 204/159.15 |
| 4,433,076 | 2/1984 | Bauer | 523/342 |
| 4,499,066 | 2/1985 | Moro | 424/19 |
| 4,587,118 | 5/1986 | Hsiao | 424/19 |
| 4,656,027 | 4/1987 | Sjoovist | 424/495 |
| 4,710,384 | 12/1987 | Rotman | 424/465 |
| 4,749,575 | 6/1988 | Rotman | 424/441 |
| 4,800,087 | 1/1989 | Mehta | 424/494 |
| 4,859,469 | 8/1989 | Baudier et al. | 424/494 |
| 4,882,169 | 11/1989 | Ventouras | 424/494 |

FOREIGN PATENT DOCUMENTS 2147501A   5/1985   United Kingdom .................. 424/16

OTHER PUBLICATIONS

Mixing of Poly(meth)acrylate Dispersions for Coating Drugs, Lehmann and Dreher, Pharm. Inc. 481, No. 10, 1182-1183.

"Eudragit E30D (NE30D)—Aqueous Acrylic Resin Dispersion", Rohm Pharma, 1984, pp. 1-7.

"Eudragit L30D,—Aqueous Acrylic Resin Dispersion", Rohm Pharma, 1983, pp. 1-7.

*Primary Examiner*—Thurman K. Page
*Assistant Examiner*—Amy Hulina
*Attorney, Agent, or Firm*—Kenyon & Kenyon

[57] ABSTRACT

In accordance with the present invention, these and other objects are achieved by a pharmaceutical composition comprised of 1) a pharmaceutical core which is further comprised of a pharmaceutically active dose of a compound and, 2) a microencapsulating polymer which coats the pharmaceutical core and is capable of taste-masking the active compound. The polymer coating maintains its integrity, i.e., does not fracture and release active when tabletted and/or chewed, and can provide immediate release of the active compound in the stomach, or alternatively, in certain embodiments, can release the active agent in the upper intestinal tract or in sustained release fashion. Additionally, the polymeric coating compositions or the pharmaceutical core may contain diluents, fillers, bulking agents, and plasticizers. The polymeric coatings may also contain pigments and opacifiers to promote compliance and enhance the storage stability of light sensitive active agents.

17 Claims, No Drawings

TASTE-MASKED PHARMACEUTICAL COMPOSITIONS

BACKGROUND OF THE INVENTION

This invention relates to novel taste-masked pharmaceuticals and to taste-masked pharmaceuticals capable of being chewed without producing a bitter taste. In one embodiment of the invention a pharmaceutical composition comprised of a coated acetaminophen core that masks the bitter and unpleasant taste of acetaminophen is provided. A method of producing chewable tablets incorporating the coated acetaminophen is also described. The coating composition and the method of producing chewable tablets may be modified to provide taste-masking properties to a large number of unpleasant tasting drugs.

In a preferred embodiment of this invention, the formulation comprises a tablet which is further comprised of acetaminophen coated with a combination of polymers. In this embodiment, the acetaminophen chewable tablets do not exhibit the bitter and unpleasant taste normally associated with acetaminophen. In other embodiments, taste-masked dosage forms comprised of a number of antibiotics, and other pharmaceutical agents are provided. In each of these embodiments, excipients and other additives may be added to aid solubility and/or compressibility.

An oral dosage form is the preferred route of administration of acetaminophen and other pharmaceutical compounds because it provides easy, low cost administration. However, patient compliance becomes an important factor, especially when administering pharmaceuticals to children. Children generally show poor compliance with non-chewable tablets. Traditional non-chewable tablets generally show poor compliance in children, because they have trouble swallowing whole tablets. Part of the solution to this compliance problem is the use of chewable tablets as the administration vehicle. Chewable tablets are quite common and popular for solving the compliance problem, but when bitter or unpleasant tasting active agents, such as acetaminophen, are to be incorporated into chewable tablets, there is a need to mask the taste of the drugs. Otherwise, whatever increased compliance is obtained by using a chewable tablet will be lost to the unpleasant taste.

Conventional taste-masking techniques, for example, sweeteners and flavoring agents, may often be used. However, when a particularly unpleasant tasting active agent is to be administered, such as acetaminophen, these traditional sweeteners or flavoring agents are not as effective as certain embodiments of the invention described herein.

Alternative approaches of the prior art include microencapsulating unpleasant tasting active agent in a coating of ethyl cellulose or a mixture of ethyl cellulose and hydroxypropyl cellulose or other cellulose derivatives to provide chewable taste-masked products. These prior art products, however, suffer from the disadvantage that the polymer coating releases the active agent in an inconsistent fashion and may not provide immediate release. This may be due to a lack of an adequate amount of plasticizer in prior art chewable capsules to provide the necessary integrity for consistent release.

To provide chewable, taste-masked capsules with consistent release qualities microencapsulation with cellulose derivatives requires a plasticizer, for example, polyethylene glycol, among others, an adequate amounts to soften the coating and provide elasticity, or chewability. Elastic qualities are highly desirable in taste-masked microcapsules, because these qualities aid the capsule to resist fracture or rupture during chewing.

In one aspect of this invention, adequate supplies of plasticizer are incorporated into the polymeric cellulose coating to provide chewable capsules of greater integrity, i.e., the ability to avoid rupture or fracture during chewing than prior art chewable cellulose coated capsules.

In a second aspect of this invention, it has surprisingly been found that the incorporation of adequate amounts of a low temperature film forming polymer with cellulose polymers or other high temperature film forming polymers into the polymeric coating of a microcapsule will provide superior elastic (chewable) and taste-masked characteristics without causing delay of drug release when combined in accordance with this invention.

From a manufacturing cost standpoint, it is desirable to have chewable, taste-masked microcapsules that are large (0.25–1 mm in diameter), because larger microcapsules are easier to manufacture and package, and are less expensive to produce than are smaller microcapsules. However, an increase in size makes fracture during chewing and the release of drug from the microcapsule more likely to occur especially when there is an inadequate amount of plasticizer or other component included to provide elasticity. A larger sized microcapsule requires greater elasticity to minimize the likelihood that a fracture will occur and active agent will be released. There is therefore a need in the art of pharmaceutical formulation to provide encapsulating coatings capable of being formulated into chewable microcapsules as large as about 1.5 mm., that will not release drugs during chewing.

Prior art chewable microcapsules also suffer from the disadvantage that they are formulated using a technique known as coacervation (phase separation). The coacervation technique itself suffers from certain disadvantages. First, the technique requires the use of hydrocarbon and other flammable organic solvents, for example, cyclohexane, which are explosive and present problems in large scale manufacturing. Second, the technique is expensive, because of the additional costs associated with the regulatory compliance (EPA) relative to the method aspect of the invention described herein. Third, the process is very sensitive, and sometimes leads to reproducibility problems.

It is therefore an object of this invention to provide an improved orally active pharmaceutical composition that serves to taste-mask active agents. It is a further object of this invention to provide a chewable tablet or capsule that taste masks pharmaceutically active agents that are unpleasant in taste to increase patient compliance, especially in children.

It is an additional object of this invention to provide a chewable taste-masked formulation that can provide immediate release of an active compound as soon as it reaches the stomach. It is an additional object of this invention to provide a taste-masked formulation in "sprinkle" form that can provide immediate release of active agent in the stomach, delayed release of the active agent in the upper intestinal tract (duodenum, jejunum, or ileum) or sustained release of the active agent.

It is an additional object of this invention to provide chewable tablets of acetaminophen which do not exhibit the bitter, unpleasant taste characteristic of acetaminophen.

It is a further object of this invention to provide a method of producing taste-masked chewable pharmaceutical formulations utilizing an aqueous based formulation and an efficient process relative to the prior art methods such as coacervation or conventional coating techniques.

SUMMARY OF THE INVENTION

In accordance with the present invention, these and other objects are achieved by a pharmaceutical composition comprised of 1) a pharmaceutical core which is further comprised of a pharmaceutically active dose of a compound and, 2) a microencapsulating polymer which coats the pharmaceutical core and is capable of taste-masking the active compound. The polymer coating maintains its integrity, i.e., does not fracture and release active when tabletted and/or chewed, and can provide immediate release of the active compound in the stomach, or alternatively, in certain embodiments, can release the active agent in the upper intestinal tract or in sustained release fashion. Additionally, the polymeric coating compositions or the pharmaceutical core may contain diluents, fillers, bulking agents, sweeteners, flavors and/or plasticizers. The polymeric coatings may also contain pigments and opacifiers to promote compliance and enhance the storage stability of light sensitive active agents.

The formulations of the present invention include pharmaceutically effective amounts of an active agent microencapsulated with a polymeric coating. In preferred chewable embodiments of this invention, the coating is insoluble or alternatively, non-swellable in the pH range that exists in the mouth. The effect of this insolubility or absence of swelling within the pH range of the mouth is to prevent release of the active agent in the mouth. Additionally, the coating may simply be of a character that will not release active agents in the limited amount of fluid that exists in the mouth during chewing. Alternatively, the pharmaceutical core size may be kept to a minimum (10 to 100 micrometers) and microencapsulated to provide pharmaceutical "sprinkles". These can be used on food and in drinks to provide an alternative administrative vehicle having immediate, enteric or sustained release characteristics.

The microcapsules of the present invention are preferably of a size and elastic character that will not fracture during chewing. After the microcapsules are swallowed, the low pH environment of the stomach or simply the large volume of aqueous fluid will dissolve or swell the polymeric coating and allow the encapsulated active agent to be released immediately, i.e., within a period of at most about two hours.

The taste-masked microcapsules of the present invention exhibit the following advantages. First, the microcapsules may be formulated by using an aqueous based system. Second, the microcapsules have characteristics which allow them to withstand chewing. The microcapsules can be tabletted without losing their taste-masking ability. Third, the microcapsules can be produced to release active agents rapidly, in the upper intestinal tract, or in sustained release fashion. Fourth, the production of the microcapsules may be performed easily, accurately, and consistently, thus eliminating the reproducibility problems of the prior art methods.

DETAILED DESCRIPTION OF THE INVENTION

The present invention comprises formulations of taste-masked microcapsules which further comprise 1) a polymeric coating that may provide chewable taste-masked characteristics, and 2) a pharmaceutical core of active ingredients. Both the polymeric coating and the pharmaceutical core may further comprise diluents, fillers and other pharmaceutical additives which may effect the rate of release of active agent(s) from the microcapsule.

Preferably, the polymeric coating composition is comprised of a mixture of polymers differing in physicochemical properties. Each of the polymers in the mixture is preferably dispersible in water so as to take advantage of aqueous formulation techniques. Aqueous-based coating systems are safe and make regulatory compliance (EPA) relatively easy compared to non-aqueous based coating systems. A number of polymeric coatings that can provide an elastic microcapsule and will not release active agent in the mouth when chewed are contemplated by the present invention.

A preferred coating composition is a mixture comprised of at least about 5% of a high temperature film forming polymer and about 5% of a low temperature film forming polymer based on the total weight of polymer in the microcapsule coating. A high temperature film forming polymer or "hard" polymer is defined as a polymer that will form a film on a pharmaceutical core at a temperature of at least about 30° C. Examples of high temperature film forming polymers useful in this invention include hydroxypropylmethyl cellulose, for example, Pharmacoat TM 606 brand from Shinetsu Corp., Tokyo, Japan, hydroxypropyl cellulose, for example, Klucel TM brand from Hercules Corp. Wilmington, Del., methylcellulose for example Methocel A TM, from Dow Chemical, Midland, Mich., ethylcellulose, for example, Ethacel TM brand from Dow Chemical Corp. and other aqueous polymeric dispersions such as Aquacoat TM Brand from FMC, Philadelphia, Penna. and Surelease TM brand from Colorcon, West Point, Penna., polyvinyl alcohol, polyvinyl acetate, cellulose acetate butyrate, styrene acrylate copolymers, for example Janocryl 138 (61° C. film forming copolymer from S. C. Johnson, Racine, Wis.) and copolymers of acrylic acid esters, for example, the Eudragit TM Copolymers (Rohm Pharma GmbH Westerstadt, W. Germany): Eudragit TM L30D, Eudragit TM L100-55, Eudragit TM RS(30D and 100D) and Eudragit TM RL(30D and 100D).

Eudragit TM copolymers that are preferred in embodiments of this invention include L30D, an anionic copolymer based on polymethacrylic and acrylic acid esters (Methacrylic Acid Copolymer, Type C- in USP XXI/NF XVI) with a mean molecular weight of 250,000, and Eudragit TM RS and RL copolymers based on poly(meth)acrylic acid esters containing a low content of quaternary ammonium groups (from tertiary amino alkyl methacrylate polymerized into the copolymer backbone) which provide for active agent permeability over a widely ranging pH.

The polymeric coating may provide for immediate release characteristics, i.e., rapid release of the active agents in the stomach within a period of at most 2 hours, enteric release, or sustained release characteristics, depending upon the type and amount of polymer selected and the mode of administration. When the microcapsules are formulated into chewable, taste-masked oral tablets or capsules, the formulations provide for immediate, rapid release in the stomach. "Sprinkle" formulations may provide for immediate release, enteric release, or sustained release.

The chewable polymeric coating providing immediate release i.e., within two hours after ingestion may be comprised of a pharmaceutically compatible high temperature film forming polymer that is water insoluble or not swellable within the pH range (about 5.5-6.5) and/or the liquid content of the mouth and will not release the active agent in the mouth, but will dissolve or change in physical character in the stomach, for example, swell or become more porous, thus releasing drug. Examples of polymers which may be used in this manner include acid sensitive polymers, and polymers that may be solubilized at low pH after chewing for example, Eudragit E100 TM (soluble at pH 2-5) or swell at low pH, for example, Eudragit TM RL and RS, thus releasing active agent in the stomach after chewing.

Another preferred high temperature film forming acrylic resin polymer that releases active agent rapidly is Eudragit L30D. Although Eudragit L30D is soluble at pH's in the mouth and insoluble at pH's of the stomach, it has found usefulness in chewable, taste-masked immediate release formulations of the present invention. This usefulness may stem from the lack of liquid in the mouth, or may be the result of elastic qualities that Eudragit TM L30D acquires when formulated in combination with a plasticizer, or preferably, with Eudragit TM E30D.

Other preferred high temperature film forming polymers are the Aquacoat TM ethyl cellulose polymers available from FMC Corporation, Philadelphia, Penna., U.S.A. which are in the form of 30% aqueous polymeric dispersion having a low particle size and narrow particle size distribution. Similar ethyl cellulose compositions which include a plasticizer are available from Colorcon Westpoint, Penna. U.S.A. under the tradename Surerelease TM.

Any of the above described high temperature film forming polymers may be used alone or in combination for microencapsulation. However, to make capsules of the required elasticity using the above described film forming polymers, plasticizers may be incorporated into the coatings. Plasticizers useful to provide the requisite elasticity include polyalkylene glycols, for example polyethylene glycol, triacetin, (glyceryl triacetate from Eastman Kodak, Rochester, N.Y.) vinyl pyrrolidone, diethyl phthallate, dibutylsebacate, and esters of citric acid, among others. Generally, the plasticizers comprise between about 2% and about 50% by weight of polymer and plasticizer combined, preferably between about 5 and 15% by weight and most preferably about 10% by weight of the polymer and plasticizer combined.

Alternatively, a low temperature film forming polymer characterized as a soft, plasticizer-like polymer may be used alone, or in combination with any of the above-described "hard" polymers to produce a polymeric coating that is elastic, maintains its integrity during chewing, and may be easily formulated into microcapsules when chewable ranging in size from about 10 microns up to about 1.5 mm in diameter. A low temperature film forming polymer or "soft" polymer is a polymer which forms a polymeric film at a temperature below about 25° C. A preferred "soft" polymer is a copolymer of methacrylic acid esters. A preferred polymethacrylic acid ester copolymer having a mean molecular weight of 800,000 is Eudragit E 30D (Rohm Pharma). Other examples of low temperature film forming polymers useful in aspects of this invention are Janocryl 77 (styrene acrylate with a film forming temperature of 20° C., available from S. C. Johnson, Racine, Wis.) and Eudragit E100 (Rohm Pharma).

The soft polymer and hard polymer may be combined to form achewable, elastic microcapsule exhibiting immediate release characteristics. These polymers release the active agent as a function of the pH change or as a function of the increased volume of liquid in the stomach or by a diffusion process. The microcapsules preferably do not fracture while in the mouth. Immediate release is particularly useful when orally administering active agents that are readily absorbed from the stomach or do not require a gradual release of the active agent over time. This approach has been shown to be particularly effective with active agents that are absorbed from the stomach, for example, acetaminophen.

A particularly preferred combination of polymers that provides the above-mentioned immediate release characteristics in the stomach is a mixture of two copolymers, the copolymer of methacrylic acid and methacrylate, for example Eudragit TM L 30D, and the copolymer of (meth)acrylic acid ester, for example, Eudragit TM E 30D (NE30D). It has surprisingly been found that the combination of these two copolymers provides microencapsulated capsules exhibiting favorable taste-masking and chewable qualities, yet provides immediate release when exposed to the stomach juices. This is an especially surprising characteristic, because Eudragit TM L30D when formulated alone in nonchewable capsules releases the active agent in the small intestine, not the stomach.

Though not willing to be bound by theory in limiting the scope of this invention, it appears that the above-described immediate release characteristics of the combination of Eudragit TM L30D and E30D (NE30D) are the result of an interaction between the two copolymers that results in immediate release in the stomach, yet provides the necessary elasticity and integrity for taste-masking in a chewable tablet.

Alternatively, microcapsules exhibiting sustained release characteristics may be formulated as tablets and capsules, or as "sprinkles" for use on food or in drink. The polymers that are preferred for use in the sustained release aspect of this invention include those polymers which are soluble or swellable at a pH above 5, or polymers that are slowly permeable regardless of pH. Permeable acrylic copolymers, for example, Eudragit TM RS and RL polymers are especially useful and are preferred. It is also possible to combine polymers with the above-described characteristics.

Depending upon the release characteristics required, it is also possible to combine more than two polymers to form a microcapsule. For example, one preferred approach may be to combine a polymer that releases active ingredient at a low pH, i e., a pH that occurs in the stomach environment, with a polymer that releases drugs at a pH found in the small intestine (about 5.5-7.5) and a polymer that is permeable regardless of the pH of the surrounding environment.

Another effective approach may be to provide more than one type of microcapsule each differing in release qualities and differing as to the release sites. For example, a microcapsule coated with a polymer that releases an active agent at low pH can be combined with a microcapsule that releases active agent at a higher pH in the small intestine and/or a microcapsule that releases agent regardless of pH. This will result in a formulation that provides a bolus dose of an active agent to rapidly increase plasma concentration of active to effective levels and a sustained release of active to maintain the blood levels at the effective levels.

Particularly preferred embodiments of the taste-masked sustained release microcapsules are comprised of a combination of Eudragit TM RS and RL (low and high permeability trimethyl ammonium ethyl methacrylate copolymers) and Eudragit TM E30D or a combination of Eudragit TM L30D and Eudragit E30D. The amount of low permeable RS and high permeable RL copolymer can be varied as a function of the release characteristics and pharmacokinetics of the active agent. Likewise, the amount of Eudragit TM L30D and Eudragit TM E30D varies as function of the release characteristics and pharmacokinetics of the active agent. The release characteristics of the active agent from the polymeric coating will be affected by the physicochemical character of the active agent (particle size, crystallinity, solubility/lipophilicity). These polymers may lose their sustained release characteristics when chewed for a sustained period of time, and are therefore not contemplated for use in the chewable tablet as part of this invention. However, sustained release qualities of these polymer combinations are maintained in the "sprinkle" form and the non-chewable capsule/tablet aspects of this invention.

For the chewable tablet, capsule or sprinkle aspect of this invention it is preferred that each of the high temperature film forming polymers be combined with a low temperature film forming polymer, for example, Eudragit TM E30D so that the coating will have the required elasticity and integrity to endure chewing without fracturing and releasing active agent.

The polymeric coating described in detail above encapsulates a core comprised of, in part, a pharmaceutically active compound. The taste-masking embodiment of the present invention may be used with virtually any active agent, or agent combination, except those that are chemically incompatible with the polymers used. The taste-masking aspect of this invention is, of course, of greatest utility for those compounds that are especially bitter tasting and cannot be taste-masked by more traditional means. The taste-masking microcapsules are especially useful for bitter or unpleasant tasting drugs, for example, a number of antibiotics including erythromycin, penicillin, ampicillin, among others, as well as other active agents for example, acetaminophen, ibuprofen, dextromethorphan, cimetidine, pseudoephedrine, diphenhydramine, spironolactone, chlorpheniramine, theophylline, ranitidine and phenylbutazone among others and any suitable salts thereof.

An especially preferred embodiment of this invention includes acetaminophen as the active agent in a chewable tablet form of administration coated with a 50:50 mixture of Eudragit TM L30D and E30D copolymers. Acetaminophen has long been a preferred and highly successful analgesic and antipyretic agent. It is the analgesic/antipyretic agent of choice, preferred to aspirin, especially in children, because unlike aspirin, acetaminophen does not precipitate Reye Syndrome in children.

Where fast release in the upper intestinal tract or stomach is required and the high temperature film forming polymers is an ethyl cellulose polymer, e.g., Aquacoat N-2, at least about 50% wt. of the coating composition should be high temperature film forming polymer composition.

In many embodiments of this invention a diluent or bulking agent is preferably added to the core material. Acceptable diluents useful in embodiments of the present invention include dextrose, sorbitol, sucrose, lactose, and mannitol, urea, salts, for example potassium chloride, sodium chloride, salts of phosphate, gelatin, starch, the natural and synthetic cellulose derivatives including, for example methyl-, ethyl-, propyl-, hydroxymethyl, hydroxyethyl, hydroxypropyl or hydroxypropyl methyl cellulose, silica, polyvinyl alcohol, polyvinyl pyrrolidone and stearic acid and its salts for example magnesium stearate, among others. In general, the type and amount of diluent in the core material depends on the physicochemical characteristics of the active agent to be released. Another factor determining the amount and type of diluent used is the type of release, i.e., rapid or sustained that will be used to administer the active agent. The diluent generally comprises from about 0.1% to about 95% by weight of the core material, and preferably comprises between about 10% and 35% by weight of the core.

The pharmaceutically active core can be produced by a number of different prior art methods, but four approaches are preferable. In the first approach, a pharmaceutically active drug (in powder form) is first placed in a fluidized bed equipment (Glatt, model GPCG-5, Glatt Air techniques, Inc. Ramsey, N.J.) and thereafter, a spray binder solution or suspension comprised of, for example, polyvinyl pyrrolidone, starch, hydroxypropylmethyl cellulose or microcrystalline cellulose (Avicel, from FMC) among other excipients in a pharmaceutically acceptable solvent for example water, 95% ethanol, or acetone, among others is sprayed onto the powder, formed into granules and then dried until the solvent is evaporated. The drying temperature may vary over a broad range, but cannot be so high as to render the active agent inactive.

A second approach is to take powdered or granular active agent, and diluent or bulking agent and form a wet mass utilizing water or a pharmaceutically acceptable solvent, for example water, ethanol or propylene carbonate. The mixture is mixed (Hobart mixer) until a wet mass or dough is formed. The wet mass is then placed in an extruder (for example, Xtruder TM by LUWA, Inc. Charlotte, N.C.) and extruded as a long, thin strand. The mixture may then be dried or may be placed in a spheronizer, (Murmurizer TM LUWA, N.C.) which makes a pharmaceutical core that is round and dry. The drying temperature may be any temperature that does not affect the activity of the active agent, and, depending upon the agent employed, can vary over a broad range.

A third method for preparing the pharmaceutical core includes taking a pure drug in powdered or granular form and mixing a lubricant, for example magnesium stearate or talc among others, with the active agent. The lubricated mixture can then be passed through a compactor, for example, Chilsonator TM by Fitzpatrick, Co., Elmhurst, Ill. compacted into a mass, and then passed through a size reduction machine (Fitzmill TM by Fitzpatrick, Co.) and reduced to a suitable particle size.

A fourth method for preparing the pharmaceutical core includes coating pure drug in granular or crystalline form with a polymeric coating.

The pharmaceutical core is coated with a taste-masking polymer or combination of polymers utilizing fluid bed equipment. In the method of the present invention commercially available pharmaceutical granules (U.S.P. grade) of an active agent, or a pharmaceutical core produced by one of the previously disclosed methods, are placed in a fluid bed equipment utilizing, either a Wurster insert (bottom spray mode), a conventional granulating insert (top spray mode), or in a rotary granulator (tangential spray mode). The polymeric coating is an aqueous dispersion which may include plasticizers, pigments, anti-foaming agents, for example, silicone compounds and lubricants, for example talc or magnesium stearate. In addition a lacquer coating may be added in certain embodiments using the Eudragit TM acrylic resins. Plasticizers useful in certain polymeric coatings include propylene glycol, triacetin, vinylpyrrolidone, diethyl phthallate, dibutylsebacate, and citric acid esters. In general, the plasticizers, when used, comprise about 2% to about 50% by weight of the polymeric coating, and preferably comprise about 7% to about 15% of the coating. In many cases, the plasticizer preferably comprises about 10% by weight of the polymeric coating. In polymeric coatings utilizing a low temperature film forming polymer, for example, Eudragit TM E30D, Eudragit E100, or Janocryl TM 77, a plasticizer may be used, but is generally not recommended.

For pigments, titanium dioxide, iron oxide, and various color pigments including vegetable dyes may be used. As a general rule, the particle size of the pigments is preferably between 5 and 10 micrometer, and generally should not exceed 15um. Pigments are preferred when formulating chewable, taste-masked capsules because compliance may be enhanced when a capsule is attractively colored. Pigments and opacifiers are especially preferred for stabilizing and enhancing the shelf life of pharmaceutical actives that are light sensitive or unstable. When pigments or opacifiers are used, it is sometimes preferred that non-ionic plasticizers, for example, Tween 60 and 80, polyvinylpyrrolidone and polyethylene glycol, among others, be used. The amount of plasticizers used may vary, but should generally not exceed about 50%.

Once the pharmaceutical core has been coated it can then be encapsulated in a hard gelatin capsule, further coated with candy coating or pressed into tablet form or presented as a "sprinkle" dosage form. The encapsulation processes are standard dosage form well known in the pharmaceutical formulation art. The microcapsules may be encapsulated or tabletted along with flavorants and sweeteners to aid compliance. The sweeteners and flavorants encapsulated or tabletted along with the microcapsules are preferably powders, but where possible, formulations may include syrups or doughy mixtures. Preferred sweeteners include artificial sweeteners, for example, saccharin and cyclamates, the sweetener aspartame, including mixtures of aspartame and saccharin, and natural sweeteners including sucrose, fructose and glucose, among a number of mono- and disaccharides. Preferably, the sweetener comprises about 0.02% to about 75% by weight of the total tablet, depending upon the sweetener used. Of course, the amount of aspartame and saccharin used will generally be much smaller than the other sweeteners mentioned above and preferably will be less than about 0.5% of the total weight of the capsule to be administered.

Preferred flavorants useful in certain aspects of the present invention include cherry, grape, strawberry, chocolate, vanilla, spearmint, mocha, and cola among other flavorants. The amount of flavorant used in the present invention is that amount which provides a pleasant flavor and increases compliance but, in general is at most 2% by weight of the composition.

The chewable taste-masked capsules or tablets are administered in standard manner, the capsules or tablets are placed in the mouth, chewed, and then swallowed. The "sprinkle" form may be placed or sprinkled on cereal and other foods or in drinks and ingested. Non-chewable taste-masked capsules/tablets are simply administered by swallowing without chewing.

A further aspect of this invention is the method for producing the taste-masked microcapsules. In general, the method comprises dispersing coating polymers and other additives in an aqueous vehicle, spraying the coating mixture, drying the coated pharmaceutical core and then pressing the microcapsule into tablets and encapsulating the microcapsule in hard gelatin.

In a particularly preferred aspect of the method of this invention Eudragit TM E30D and Eudragit TM L30D is mixed in a 1:1 weight ratio, and sprayed onto fluidized acetaminophen pharmaceutical cores comprised of granular acetaminophen.

The preferred amount of applied coating is 20 to 40% of the total weight of the microcapsules when the coating is to be applied by the top spray, bottom spray and tangential spray techniques.

Illustrating the invention are the following examples. These examples are for aiding the understanding of the invention, and are not to be construed as limiting the invention to their details.

A mixture consisting of Eudragit L30D and Eudragit E30D in equal portions (50:50) is sprayed onto the fluidizing acetaminophen particles. Eudragit TM L30D supplied as an aqueous dispersion containing 30% w/w of dry lacquer substance (Rohm-Pharma) is mixed with Eudragit TM E30D, also supplied as a 30% w/w dispersion in a 1:1 ratio and placed in a suitable container and sprayed onto the fluidized particles using Glatt equipment (model GPCG5 Glatt Air Techniques, Ramsey, N.J.).

Although a 1:1 mixture of Eudragit TM E30D and Eudragit TM L30D is most preferred, ratios ranging from 30 to 70% Eudragit TM E30D and 30 to 70% Eudragit L30D are also preferred. Ratios ranging from 5 to 95% Eudragit TM E30D and about 5 to 95% Eudragit TM L30D are also useful.

Mixtures comprising Eudragit TM NE30D and Aquacoat in three different proportions (50/50, 70/30 and 30/70 w/w) were separately sprayed onto fluidizing acetaminophen particles. Both Eudragit TM NE30D and Aquacoat are supplied as aqueous dispersions each containing about 30% w/w dry polymer.

The preferred amount of applied coating is 20 to 40% by weight of the microcapsules when applied by the top spray, bottom spray or tangential spray techniques. The preferred uncoated acetaminophen particle size range is 150 to 300 micrometers.

EXAMPLE 1.

Preparation of Coated Taste-Masked Acetaminophen Particles

|  | (Top Spray) | (Bottom Spray) | (Tangential Spray) |
|---|---|---|---|
| Acetaminophen granular, USP | 4.0 kg | 4.0 kg | 4.0 kg |
| Eudragit L30D | 2.666 kg | 2.0 kg | 2.0 kg |
| Eudragit E30D | 2.666 kg | 2.0 kg | 2.0 kg |

Preparation: Mix Eudragit L30D and Eudragit E30D at a slow agitation and spray while stirring onto the fluidized acetaminophen particles. Dry at a suitable temperature below about 60° C.

EXAMPLE 2.

Preparation of Chewable Tablets

| Coated Acetaminophen | 415 g (77.1% potent) | 384 g (83.3% potent) |
|---|---|---|
| Inactive blend | 1104 g | 1132 g |
| Lubricant (magnesium stearate or stearic Acid) | 15.6 g | 15.6 g |

Preparation: Combine inactive ingredients and lubricant together and mix well. Add acetaminophen and mix until homogeneous for about five minutes in a planetary mixer (Hobart mixer). Compress to a tablet weight of 383 mg or to a weight which would provide the desired amount of acetaminophen per tablet. The inactive blend consists of commonly used tablet excipients such as mannitol, sorbitol, microcrystalline cellulose, fructose, sweetener and flavors.

EXAMPLE 3

Preparation of Coated Taste-Masked Acetaminophen Particles

|  | I | II | III |
|---|---|---|---|
| Acetaminophen granular, USP | 1.0 kg | 1.0 kg | 1.0 kg |
| Eudragit TM NE30D | 0.5 kg | 0.7 kg | 0.3 kg |
| Aquacoat | 0.5 kg | 0.3 kg | 0.7 kg |

Preparation: Mix Eudragit TM NE30D and Aquacoat at a slow agitation and spray while stirring onto the fluidized acetaminophen particles. Dry at a suitable temperature below 60° C.

EXAMPLE 4

Preparation of Chewable Acetaminophen Tablets

Tablets with three different compositions I, II and III described in Example 3 were prepared in accordance with Example 2.

Dissolution studies were performed on each of tablets I, II and III in accordance with U.S.P. XXI Methods described at page 1694, Supplement I. The results of these dissolution studies compositions I, II and III are presented below in Table I.

TABLE I

DISSOLUTION OF CHEWABLE 80 Mg. APAP TABLETS
PERCENT DISSOLVED

| TIME | Compositions | | |
|---|---|---|---|
|  | I | II | III |
| 10 | 4.4 | 3.8 | 8.7 |
| 30 | 39.3 | 22.2 | 67.4 |
| 45 | 67.5 | 35.1 | 91.1 |
| 60 | 84.1 | 44.4 | 95.5 |
| 75 | 72.4 | 52.6 | 96.1 |
| 90 | 97.9 | — | 96.3 |

The data presented in Table I shows that coating compositions including less than about 50% low temperature film forming polymers dissolve quickly to provide immediate release in the upper intestinal tract.

I claim:

1. A chewable taste-masked pharmaceutical composition having controlled release characteristics, comprising:
   (a) a microcapsule of about 10 microns to about 1.5 mm in diameter having a core including a pharmaceutically active agent and a polymer mixture coating having sufficient elasticity to withstand chewing;
   (b) said polymeric mixture comprising
      (i) about 50% by weight ethyl cellulose that forms a polymeric film at temperatures of at least about 30° C.; and
      (ii) about 50% by weight of a low temperature film forming copolymer selected from the group consisting of methacrylic acid ester copolymers and styrene acrylate copolymers that form a polymeric film at temperatures less than about 25° C.; and
   said coating being adapted to release said pharmaceutically active agent in the stomach.

2. The composition according to claim 1 wherein the low temperature film forming polymer comprises a polymethacrylic acid ester copolymer having a mean molecular weight of about 800,000.

3. The composition according to claim 1, wherein said core further comprises a diluent.

4. The composition according to claim 1, wherein said polymer coating further comprises a plasticizer.

5. The composition according to claim 3, wherein said plasticizer is selected from the group consisting of polyethylene glycol, triacetin, vinylpyrrolidone, diethyl phthallate, dibutylsebacate, and citric acid esters.

6. The composition according to claim 1, wherein said pharmaceutically active agent is selected from the group consisting of erythromycin, penicillin, ampicillin, acetaminophen, ibuprofen, dextromethorphan, cimetidine, pseudoephedrine, diphenhydramine, spironolactone, chlorpheniramine, theophylline, phenylbutazone and ranitidine.

7. The composition according to claim 5 wherein the high temperature film forming copolymer is water soluble.

8. A chewable taste-masked pharmaceutical composition according to claim 1, wherein the polymeric mixture comprises about 70% by weight ethyl cellulose polymer aqueous dispersion and about 30% by weight of said low temperature film forming polymer, said coating being adapted to release said pharmaceutically active agent in the stomach.

9. A chewable taste-masked pharmaceutical composition having rapid release characteristics in the upper intestinal tract, comprising:
  (a) a microcapsule of about 10 microns to about 1.5 mm in diameter having a core including a pharmaceutically active agent and a polymer mixture coating having sufficient elasticity to withstand chewing;
  (b) said polymeric mixture comprising
    (i) at least about 50% by weight of a high temperature film forming copolymer comprising an aqueous ethyl cellulose polymer dispersion, that forms a polymeric film at temperatures of at least about 30° C.; and
    (ii) a low temperature film forming polymer that forms a polymeric film at temperatures less than about 25° C.

10. A chewable taste-masked pharmaceutical composition according to claim 9 wherein the polymeric mixture comprises about 50% by weight ethyl cellulose polymer aqueous dispersion and about 50% by weight of said low temperature film forming polymer, said coating being adapted to release said pharmaceutically active agent in the stomach.

11. The composition according to claim 9 wherein the low temperature film forming polymer comprises a polymethacrylic acid ester copolymer having a mean molecular weight of about 800,000.

12. The composition according to claim 9, wherein said core further comprises a diluent.

13. The composition according to claim 9, wherein said polymer coating further comprises a plasticizer.

14. The composition according to claim 12, wherein said plasticizer is selected from the group consisting of polyethylene glycol, triacetin, vinylpyrrolidone, diethyl phthallate, dibutylsebacate, and citric acid esters.

15. The composition according to claim 9, wherein said pharmaceutically active agent is selected from the group consisting of erythromycin, penicillin, ampicillin, acetaminophen, ibuprofen, dextromethorphan, cimetidine, pseudoephedrine, diphenhydramine, spironolactone, chlorpheniramine, theophylline, phenylbutazone and ranitidine.

16. The composition according to claim 9, wherein the coating provides immediate release in the stomach of the active agent in the core.

17. A chewable taste-masked pharmaceutical composition according to claim 9, wherein the polymeric mixture comprises about 70% by weight ethyl cellulose polymer aqueous dispersion and about 30% by weight of said low temperature film forming polymer, said coating being adapted to release said pharmaceutically active agent in the stomach.

* * * * *

UNITED STATES PATENT AND TRADEMARK OFFICE
CERTIFICATE OF CORRECTION

PATENT NO. : 5,084,278
DATED : January 28, 1992
INVENTOR(S) : Atul M. Mehta

It is certified that error appears in the above-identified patent and that said Letters Patent is hereby corrected as shown below:

Abstract, line 9, after "active" add --compound--.

Column 1, line 68, change "an" to --in--.

Column 3, line 20, after "active" add --compound--.

Column 7, line 5, after "active" add --compound--.

Column 12, line 59, change "5" to --1--.

Signed and Sealed this

Twenty-second Day of June, 1993

Attest:

MICHAEL K. KIRK

*Attesting Officer*     *Acting Commissioner of Patents and Trademarks*